(12) United States Patent
Shooshtari et al.

(10) Patent No.: US 8,652,579 B2
(45) Date of Patent: Feb. 18, 2014

(54) PROCESSES OF MAKING FIBER-CONTAINING COMPOSITES FROM POLYAMIC ACID-CONTAINING BINDER COMPOSITIONS

(75) Inventors: Kiarash Alavi Shooshtari, Littleton, CO (US); Jawed Asrar, Englewood, CO (US)

(73) Assignee: Johns Manville, Denver, CO (US)

( * ) Notice: Subject to any disclaimer, the term of this patent is extended or adjusted under 35 U.S.C. 154(b) by 0 days.

(21) Appl. No.: 13/313,232

(22) Filed: Dec. 7, 2011

(65) Prior Publication Data

US 2012/0088032 A1     Apr. 12, 2012

Related U.S. Application Data

(62) Division of application No. 11/799,904, filed on May 3, 2007, now abandoned.

(51) Int. Cl.
*D06M 13/224* (2006.01)
*B32B 27/00* (2006.01)

(52) U.S. Cl.
USPC ............... 427/385.5; 427/389.9; 427/389.7; 427/389.8; 428/375

(58) Field of Classification Search
USPC .................. 427/385.5, 389.9, 389.7, 389.8; 428/375
See application file for complete search history.

(56) References Cited

U.S. PATENT DOCUMENTS

| | | | |
|---|---|---|---|
| 3,245,933 A | 4/1966 | Muskat | |
| 3,908,048 A | 9/1975 | Kawanaka et al. | |
| 3,939,108 A * | 2/1976 | Sirota et al. ................. | 524/52 |
| 5,143,582 A | 9/1992 | Arkens et al. | |
| 5,318,990 A | 6/1994 | Strauss | |
| 5,340,868 A | 8/1994 | Strauss | |
| 5,427,587 A | 6/1995 | Arkens et al. | |
| 5,661,213 A | 8/1997 | Arkens et al. | |
| 6,136,916 A | 10/2000 | Arkens et al. | |
| 6,221,973 B1 | 4/2001 | Arkens et al. | |
| 6,331,350 B1 | 12/2001 | Taylor et al. | |
| 6,452,030 B1 | 9/2002 | Chosa et al. | |
| 6,706,853 B1 | 3/2004 | Stanssens et al. | |

FOREIGN PATENT DOCUMENTS

| | | |
|---|---|---|
| DE | 12 89 934 B | 2/1969 |
| DE | 198 05 136 A1 | 8/1999 |
| WO | 2007/149643 A1 | 12/2007 |

OTHER PUBLICATIONS

Arkins, Charles T., et al., Formaldehyde-Free Crosslinking Binders for Non-Wovens, Tappi Journal, vol. 78, No. 11, pp. 161-168, Nov. 1995.

Shooshtari, Kiarash Alavi, PhD Dissertation entitled "Michael Addition of Amines to Alpha-beta Unsaturated Esters".

* cited by examiner

*Primary Examiner* — Robert D. Harlan
(74) *Attorney, Agent, or Firm* — Robert D. Touslee

(57) ABSTRACT

Processes are described for binding a fibrous material. The processes may include applying to a surface of the fibrous material an aqueous binding composition to form a coated fibrous material. The binding composition may include: (a) a water-soluble polyamic acid, and (b) an organic crosslinking agent capable of undergoing a covalent crosslinking reaction with the water-soluble polyamic acid when heated. The water-soluble polyamic acid may be formed by the reaction of: a (i) a polycarboxylic acid or polyanhydride having a molecular weight of at least 150 g/mol, and (ii) ammonia or an amine compound. The processes may further include heating the coated fibrous material to crosslink the water-soluble polyamic acid with the organic crosslinking agent to form a cured binder. One or more adjoining fibers of the fibrous material may be bound to each other at cross over points by the cured binder.

35 Claims, No Drawings

PROCESSES OF MAKING FIBER-CONTAINING COMPOSITES FROM POLYAMIC ACID-CONTAINING BINDER COMPOSITIONS

CROSS-REFERENCES TO RELATED APPLICATIONS

This is a divisional application of prior U.S. patent application Ser. No. 11/799,904 filed May 3, 2007, the entire contents of which are hereby incorporated by this reference for all purposes.

BACKGROUND OF THE INVENTION

1. Field of the Invention

The subject invention pertains to an improved aqueous binding composition for use with fibrous materials. More specifically, the subject invention pertains to the use of a curable binding composition comprising a water-soluble polyamic acid and an organic crosslinking capable of reaction with the polyamic acid. Such polyamic acid is formed by the reaction of a polycarboxylic acid and/or polyanhydride having a molecular weight of at least 150 and ammonia and/or an amine compound. The aqueous binding composition is coated on a fibrous material and is heated to achieve crosslinking to form a water-resistant cured binder in association with the fibrous material wherein adjoining fibers are bound at cross-over points.

2. Description of the Related Art

Binders for fibrous materials, such as fiberglass, have a variety of uses ranging from stiffening applications where the binder is applied to woven or non-woven fiberglass sheet goods and is cured, producing a stiffer product; thermo-forming applications wherein the binder resin is applied to a sheet or lofty fibrous product, following which it is dried and optionally is B-staged to form an intermediate but yet curable product; and to fully cured systems such as building insulation.

Fibrous glass insulation products generally comprise matted glass fibers bonded together by a cured thermoset polymeric material. Molten streams of glass are drawn into fibers of random lengths and are blown into a forming chamber where they are randomly deposited as a mat onto a traveling conveyor. The fibers, while in transit in the forming chamber and while still hot from the drawing operation, are sprayed with an aqueous binder. A phenol-formaldehyde binder has been used throughout the fibrous glass insulation industry. The residual heat from the glass fibers and the flow of air through the fibrous mat during the forming operation are generally sufficient to volatilize water from the binder, thereby leaving the remaining components of the binder on the fibers as a viscous or semi-viscous high solids liquid. The coated fibrous mat is transferred to a curing oven where heated air, for example, is blown through the mat to cure the binder and rigidly bond the glass fibers together.

Fiberglass binders used in the present sense should not be confused with matrix resins which are an entirely different and non-analogous field of art. While sometimes termed "binders", matrix resins act to fill the entire interstitial space between fibers, resulting in a dense, fiber reinforced product where the matrix must translate the fiber strength properties to the composite, whereas "binder resins" as used herein are not space-filling, but rather coat only the fibers, and particularly the junctions of fibers. Fiberglass binders also cannot be equated with paper or wood product "binders" where the adhesive properties are tailored to the chemical nature of the cellulosic substrates. Many such resins are not suitable for use as fiberglass binders. One skilled in the art of fiberglass binders would not look to cellulosic binders to solve any of the known problems associated with fiberglass binders or binders for use on similar fibrous materials.

Binders useful in fiberglass insulation products generally require a low viscosity in the uncured state, yet possess characteristics so as to form a rigid thermoset polymeric mat for the glass fibers when cured. A low binder viscosity in the uncured state is required to allow the mat to be sized correctly. Also, viscous binders tend to be tacky or sticky and hence they lead to the unwanted accumulation of fiber on the forming chamber walls. This accumulated fiber may later fall onto the mat causing dense areas and product problems. A binder which forms a rigid matrix when cured is required so that a finished fiberglass thermal insulation product or similar product, when compressed for packaging and shipping, will recover somewhat to its as-made vertical dimension when installed in a building.

From among the many thermosetting polymers, numerous candidates for suitable thermosetting fiberglass binder resins exist. However, binder-coated fiberglass products are often of the commodity type, and thus cost becomes a driving factor, generally ruling out in some instances such resins as thermosetting polyurethanes, epoxies, and others. Due to their excellent cost/performance ratio, the resins of choice in the past have been phenol-formaldehyde resins. Phenol-formaldehyde resins can be economically produced, and can be extended with urea prior to use as a binder in many applications. Such urea-extended phenol-formaldehyde binders have been the mainstay of the fiberglass insulation industry for years, for example.

Over the past several decades however, minimization of volatile organic compound emissions (VOCs) both on the part of the industry desiring to provide a cleaner environment, as well as by government regulation, has led to extensive investigations into not only reducing emissions from the current formaldehyde-based binders, but also into candidate replacement binders. For example, subtle changes in the ratios of phenol to formaldehyde in the preparation of the basic phenol-formaldehyde resole resins, changes in catalysts, and addition of different and multiple formaldehyde scavengers, has resulted in considerable improvement in emissions from phenol-formaldehyde binders as compared with the binders previously used. However, with increasingly stringent government regulations, more and more attention has been paid to alternative binder systems which lack formaldehyde.

One such candidate binder system employs polymers of acrylic acid as a first component, and a polyol such as glycerine or a modestly oxyalkylated glycerine as a curing or "crosslinking" component. The preparation and properties of such poly(acrylic acid)-based binders, including information relative to the VOC emissions, and a comparison of binder properties versus urea formaldehyde binders is presented in "Formaldehyde-Free Crosslinking Binders For Non-Wovens", Charles T. Arkins et al., TAPPI JOURNAL, Vol. 78, No. 11, pages 161-168, November 1995. The binders disclosed by the Arkins article, appear to be B-stageable as well as being able to provide physical properties similar to those of urea-formaldehyde resins.

U.S. Pat. No. 5,340,868 discloses fiberglass insulation products cured with a combination of a polycarboxy polymer, a beta-hydroxyalkylamide, and at least one trifunctional monomeric carboxylic acid, such as citric acid. The specific polycarboxy polymers disclosed are poly(acrylic acid) polymers. See also, U.S. Pat. No. 5,143,582 U.S. Pat. No. 5,318, 990 discloses a fibrous glass binder which comprises a polycarboxy polymer, a monomeric trihydric alcohol and a catalyst comprising an alkali metal salt of a phosphorous-containing organic acid.

Published European Patent Application EP 0 583 086 A1 appears to provide details of polyacrylic acid binders whose cure is catalyzed by a phosphorus-containing catalyst system as discussed in the Arkins article previously cited. Higher molecular weight poly(acrylic acids) are stated to provide polymers exhibiting a more complete cure. See also U.S. Pat. Nos. 5,661,213; 5,427,587; 6,136,916; and 6,221,973.

Some polycarboxy polymers have been found useful for making fiberglass insulation products. Problems of clumping or sticking of the glass fibers to the inside of the forming chambers during the processing, as well as providing a final product that exhibits the recovery and rigidity necessary to provide a commercially acceptable fiberglass insulation product, have been overcome. See, for example, U.S. Pat. No. 6,331,350. The thermosetting acrylic resins have been found to be more hydrophilic than the traditional phenolic binders, however. This hydrophilicity can result in fiberglass insulation that is more prone to absorb water, thereby possibly compromising the integrity of the product. Also, the thermosetting acrylic resins now being used as binding agents for fiberglass have been found to not react as effectively with silane coupling agents of the type traditionally used by the industry. The addition of silicone as a hydrophobing agent results in problems when abatement devices are used that are based on incineration. Also, the presence of silicone in the manufacturing process can interfere with the adhesion of certain facing substrates to the finished fiberglass material. Overcoming these problems will help to better utilize polycarboxy polymers in fiberglass binders.

U.S. Pat. No. 6,706,853 discloses a reaction product of a cyclic anhydride and an alkanolamine for use when binding fiberglass. Representative cyclic anhydrides include anhydride polymers of maleic anhydride with styrene and with methacrylate monomers.

It is an object of the invention to provide an improved binding composition for use when binding fibrous materials in the absence of the use of a phenol-formaldehyde binder.

It is an object of the invention to provide an improved process for binding a fibrous material to provide an improved water-resistant cured binder in association with a fibrous material wherein adjoining fibers are bound at cross-over points.

It is a further object of the present invention to provide a bound fibrous material wherein adjoining fibers are bound at cross-over points by means of the cured water-resistant binder of the present invention.

Other objects and advantages of the invention will be apparent to those skilled in the art upon a review of the following description and appended claims.

BRIEF SUMMARY OF THE INVENTION

An aqueous binding composition is provided for a fibrous material comprising (a) a water-soluble polyamic acid formed by the reaction of (i) a polycarboxylic acid and/or polyanhydride having a molecular weight of at least 150 and (ii) ammonia and/or amine compound, and (b) an organic crosslinking agent capable of undergoing a covalent crosslinking reaction with the water-soluble polyamic acid when heated.

A process is provided for binding a fibrous material comprising:
(1) applying to a fibrous material as a coating an aqueous binding composition comprising (a) a water-soluble polyamic acid formed by the reaction of (i) a polycarboxylic acid and/or polyanhydride having a molecular weight of at least 250 and (ii) ammonia and/or amine compound, and (b) an organic crosslinking agent capable of undergoing a covalent crosslinking reaction with the water-soluble polyamic acid when heated, and
(2) heating the coated fibrous material to achieve crosslinking of the polyamic acid to form a water-resistant cured binder in association with the fibrous material wherein adjoining binders are bound at cross-over points.

A fibrous material is provided that is coated with a water-resistant cured binder formed in accordance with the process of the present invention wherein adjoining fibers are bound at cross-over points. Such bound fibrous material is free of a phenol-formaldehyde resin.

DETAILED DESCRIPTION OF THE INVENTION

The aqueous binding composition for a fibrous material according to the present invention comprises a water-soluble polyamic acid and an organic crosslinking agent capable of undergoing a covalent crosslinking reaction therewith when heated.

The water-soluble polyamic acid is formed by the reaction of (i) a polycarboxylic acid and/or polyanhydride having a molecular weight of at least 250 and (ii) ammonia and/or an amine compound. The polycarboxylic acid and/or anhydride commonly has a molecular weight of 150 to 1,000,000, preferably approximately 1,000 to 10,000, and most preferably approximately 1,000 to 5,000. The polycarboxylic acids have at least two carboxylic acid groups and the polyanhydrides have at least two anhydride groups.

In preferred embodiments the polycarboxylic acid is a homopolymer or copolymer of any of acrylic acid, methacrylic acid, maleic acid, fumaric acid, crotonic acid, and mixtures thereof. Representative polycarboxylic acids include polyacrylic acid, polymethacrylic acid, polycrotonic acid, polyfumaric acid, polymaleic acid, poly-2-methyl maleic acid, polyitaconic acid, poly-2-methyl itaconic acid, poly-alpha-beta-methylene glutaric acid, polystyrene maleic acid, polystyrene-co-acrylic acid, polyethylene-co-acrylic acid, polyethylene-co-maleic acid, polybutadiene-co-maleic acid, etc., and copolymers of the foregoing. Copolymer units can be included in such polycarboxylic acids that are derived from other unsaturated molecules that are capable of undergoing polymerization with unsaturated acids.

Representative polyanhydrides include polyacrylic anhydride, polymethacrylic anhydride, pyromellitic anhydride, poly(acrylic-co-methacrylic)anhydride, poly(acrylic-co-maleic)anhydride, poly(methacrylic-co-maleic)anhydride, polycrotonic anhydride, polymaleic anhydride, poly(styrene-maleic)anhydride, poly(ethylene-maleic)anhydride, poly(propylene-maleic)anhydride, poly(vinylether-maleic)anhydride, poly(butadiene-maleic) anhydride, poly(acrylamide-maleic)anhydride, malienated oils, and mixtures of the foregoing. The malienated oils are formed by the reaction of unsaturated oils with maleic anhydride. Other copolymer units can be similarly present within the polyanhydrides. A preferred polyanhydride is poly(styrene-maleic)anhydride.

Other than ammonia representative amines for reaction with the polycarboxylic acid and/or polyanhydride are primary and secondary amines. Such amines may be aliphatic, aromatic or a combination of aliphatic and aromatic. Additionally, the amine compounds optionally can include other functional groups. A representative functionalized amine is glycine (i.e., aminoacetic acid). Preferred primary alkylamines are methylamine, propylamine, n-butylamine, t-butylamine, hexylamine, benzylamine, etc. Preferred secondary alkylamines are dimethylamine, dipropylamine, methylethyl amine, dihexylamine, etc. Other amines including analine, hydrazine, morpholine, piperidine, piperazine, dicyclohexylamine, N-methylaniline, imidazole-4-acrylic acid, and other amino acids, can be utilized during the formation of the polyamic acid. Mixtures of amine compounds can be utilized.

The polyamic acid commonly is formed by heating reactants (i) and (ii) while in admixture in an aqueous medium at a temperature below 100° C., and preferably at a temperature of approximately 30 to 95° C. for 10 to 240 minutes. The resulting polyamic acid possesses both reactive amide and carboxylic acid groups, and can be provided at least partially as an ammonia or amine salt.

Next the polyamic acid and the organic crosslinking capable of undergoing a crosslinking reaction with the polyamic acid when heated are applied from an aqueous binding composition as a coating on the fibrous material that is to be bound. Commonly the organic crosslinking agent is a polyol, polyamine, polyalkanolamine, or mixtures of these. Any organic crosslinking reaction can be utilized which has the ability to react with carboxylic acids and/or amides. Such organic crosslinking agents commonly are water-soluble. Representative organic crosslinking agents include glycols, glycol ethers, polyamines, alkanolamines, polyester polyols, polyether polyols, acrylic polyols, urethane polyols, polysaccharides, polyvinyl alcohol, epoxies, and mixtures thereof. Representative polyamines include hexanediamine, ethylenediamine, melamine, diethylenetriamine, triethylenetetramine, aminoaniline, aminoamides, etc. Representative alkanolamines include monoethanolamine, diethanolamine, triethanolamine, and mixtures thereof. Trimethylol propane, pentaerythritol, ethylene glycol, and triethylene glycol also are representative of suitable organic crosslinking agents.

In a preferred embodiment the organic crosslinking agent is a water-soluble Michael adduct crosslinking agent having reactive hydroxyl end groups formed by the addition reaction of a Michael acceptor compound having alpha-beta unsaturation attached to an electron-withdrawing group and a nucleophilic compound serving as a Michael donor capable of reaction with the Michael acceptor. Such Michael adduct is capable of undergoing a covalent crosslinking reaction with the water-soluble polyamic acid. This embodiment is in accordance with the teachings of U.S. patent application Ser. No. 11/799,903, to Shooshtari, filed May 3, 2007, and entitled "Binding Fibrous Material Utilizing a Water-Soluble Michael Adduct Crosslinking Agent and Polycarboxylic Acid". This United States patent application is incorporated herein by reference.

Such Michael acceptors may include at least one vinyl group (i.e., one or more vinyl groups) attached to the electron-withdrawing groups. Representative electron-withdrawing groups include ester groups, acid groups, amide groups, nitro groups, nitrile groups, ketone groups, aldehyde groups, and mixtures of these.

Representative Michael acceptors in the form of alpha-beta unsaturated esters include acrylates, such as ethyl acrylate, propyl acrylate, hydroxy ethyl acrylate, triethylene glycol diacrylate, trimethylolpropane triacrylate, pentaerythrytol tetraacrylate, epoxy acrylates such as bisphenol-A epoxy acrylate, epoxidized oil acrylate, styrene maleic anhydride acrylate, polyester polyol polyacrylates, polyurethane acrylates, metallic acrylates such as zinc diacrylate, polyamide acrylates, acryloyl propane triethoxy silane, di- and poly (dimethyl silanol)diacrylate, etc.; methacrylates, such as methyl methacrylate, hydroxy ethyl methacrylate, triethylene glycol dimethacrylate, trimethylol propane trimethacrylate, epoxy methacrylates, polyester methacrylates, polyurethane methacrylates, polyamide methacrylates, styrene maleic anhydride methacrylate, etc.; crotonates, such as methyl crotonate, hydroxy ethyl crotonate, epoxy crotonates, urethane crotonates, polyether crotonates, polyester crotonates, etc.; maleates, such as monomethyl maleate, dimethyl maleate, monohydroxy ethyl maleate, dihydroxy ethyl maleate, unsaturated esters containing maleate functionalities, epoxy maleate esters, etc.; fumarates, such as dimethyl fumarate, monohydroxy ethyl fumarate, dihydroxy ethyl fumarate, unsaturated esters containing fumarate functionalities, epoxy fumarate esters, etc.

Representative Michael acceptors in the form of alpha-beta unsaturated acids include acrylic acid, methacrylic acid, crontic acid, maleic acid, fumaric acid, 2-methyl maleic acid, itaconic acid, 2-methyl itaconic acid, propiolic acid, acetylene dicarboxylic acid, etc.

Representative Michael acceptors in the form of alpha-beta unsaturated amides include acrylamide, methacrylamide, etc.

Representative Michael acceptors in the form of alpha-beta unsaturated nitro compounds include vinyl nitrate, nitro ethylene, nitro acetylene, etc.

Representative Michael acceptors in the form of alpha-beta unsaturated nitrile compounds include acrylonitrile, methacrylonitrile, crotonitrile, etc.

Representative Michael acceptors in the form of alpha-beta unsaturated ketone compounds include methyl vinyl ketone, ethyl vinyl ketone, etc.

Representative Michael acceptors in the form of alpha-beta unsaturated aldehyde compounds include acrolein, methyl acrolein, etc.

The alpha-beta unsaturated Michael acceptor optionally may include additional chemical functionalities such as ether groups, ester groups, epoxy groups, urethane groups, urea groups, aliphatic hydrocarbon groups, aromatic hydrocarbon groups, etc. Michael acceptors in the form of oligomers of glycols and polyols may be utilized.

Maleic anhydride, acrylic anhydride, etc. also can be utilized as the Michael acceptor when forming the Michael adduct crosslinking agent.

The Michael acceptors readily undergo an addition reaction with a nucleophilic compound serving as a Michael donor through covalent bonding to form a water-soluble Michael adduct crosslinking agent having reactive hydroxyl groups. In preferred embodiments the Michael donor utilized to form the water-soluble Michael adduct crosslinking agent is an alkylamine, an alkanolamine, a thiol, and mixtures of these. Representative amines are butyl amine, ethylene diamine, 1,6-hexane diamine, diethylene triamine, amino amides, p-amino phenol, melamine, etc. Preferred amines are mono- or di-alkanolamines having 2 to 4 carbon atoms per alkanol group. Representative mono-alkanolamines include ethanolamine, propanolamine, butanolamine and N-methylethanolamine. Representative di-alkanolamines include diethanol amine, dipropanol amine, disopropyl amine, and dibutanol amine. A particularly preferred amine Michael donor is dialkanolamine. Representative thiol Michael donors are hydroxy ethyl thiol, hydroxy propyl thiol, etc.

The water-soluble Michael adduct crosslinking agent may be formed by reacting the Michael acceptor and the Michael donor in 1:1 molar proportions with stirring at a temperature of ambient to 95° C. over a period of approximately 10 to 360 minutes. In some embodiments the Michael adduct optionally can be at least partially present as a salt. The resulting Michael adduct in addition to being water-soluble commonly possesses a low viscosity of approximately 5 to 500 cps (preferably approximately 9 to 100 cps) when dissolved in water in a concentration of 50 percent by weight, a low surface tension of approximately 5 to 50 N/m (preferably 10 to 30 N/m) when dissolved in water in a concentration of 10 percent by weight, a low melting point of approximately −50 to 150° C. (preferably −20 to 100° C.), and a low vapor pressure of lower than 1.0 mm Hg. Such Michael adducts commonly can be formed on a relatively economical basis and can readily be processed and handled by workers.

The resulting water-soluble Michael adduct commonly displays a hydroxy equivalent of approximately 50 to 1000, and preferably approximately 70 to 150 as determined by titration or spectroscopy.

Optionally, the coating composition prior to crosslinking may include a minor concentration of aliphatic or aromatic lower molecular weight dicarboxylic, tricarboxylic or tetracarboxylic acids, such as adipic acid, maleic acid, terephthalic acid, isophthalic acid, trimellitc acid, pyromellitic acid, butane tetra carboxylic acid, citric acid, ethylenediamine tetraacetic acid, benzophenone tetracarboxylic acid, etc., in a concentration not to exceed approximately 20 percent on a molar basis of the polycarboxylic acid having a molecular weight of at least 250. In this embodiment the presence of such lower molecular weight carboxylic acid serves to lower the viscosity of the solution and to further aid the wetting and coverage of surface of fibrous material.

The aqueous binding composition of the present invention comprising (a) a water-soluble polyamic acid and (b) organic crosslinking agent optionally further may include polymeric emulsion components, adhesion promoters, coupling agents, oxygen scavengers, solvents, emulsifiers, pigments, anti-migration aids, UV absorbers, biocides, anti-foaming agents, colorants, dyes, anti-static agents, antioxidants, etc.

When the binding composition is coated on the fibrous material from a water solution, the mass ratio of organic crosslinking agent to water-soluble polyamic acid commonly is approximately 1:10 to 10:1, preferably approximately 1:5 to 5:1, and most preferably approximately 1:3 to 3:1.

The fibrous material to which the aqueous binding composition is applied can be provided in various configurations. The plurality of fibrous components of the fibrous material can be continuous or discontinuous. For instance, the fibers can be mineral fibers, organic fibers, or polymeric fibers. The fibrous material conveniently can be provided in mat form or in any other configuration amenable for the intended end use. The bound fibrous material (e.g. mat) can serve as fibrous reinforcement in ceiling tiles or floor tiles. For instance, the bound fibers in accordance with the present invention can be incorporated in a polyvinylchloride or other matrix during the formation of flooring tiles. Also, the bound fibrous mat can serve as fibrous reinforcement when manufacturing shingles (e.g. asphalt shingles). Representative polymeric fibers include polyethylene terphthalate or polypropylene fibers which are provided in the form of a spun-bonded mat. In a preferred embodiment the fibrous material comprises glass fibers, and preferably fiberglass fibers that are supplied as long multifilamentary rovings or tows of infinite length. The filament diameters can be adjusted to meet the needs of the requirements of specific end uses. In a preferred embodiment, the fibrous material is fiberglass for the production of building insulation. In other embodiments the fibrous product is a microglass-based substrate useful for a fiberglass printed circuit board, battery separator, filter stock, or reinforcement scrim.

The binder composition product can be applied to the fibrous material as a coating by any technique capable of coating the individual fibrous components thereof. For instance, when the fibrous material is provided in a continuous length, a kiss-roll applicator, curtain coater, deep coating, spray coating, etc. can be utilized.

Once the fibrous material is coated with the aqueous binding composition heat is applied in order to achieve crosslinking of the reactive carboxylic acid and amide groups of the polyamic acid and the organic crosslinking agent to form a water-resistant cured binder in association with the fibrous material wherein adjoining fibers are bound at cross-over points. Such heating commonly is conducted at a temperature of approximately 160 to 250° C., and preferably at a temperature of approximately 200° C. Representative times for such heating commonly are at least 0.5 minutes (e.g., approximately 0.5 to 10 minutes), and preferably approximately 1 to 3 minutes. During such heating the aqueous component of the binding composition is volatized and the individual fibers are securely bound to each other.

The quantity of binder present in the resulting bound product can be adjusted to vary with the needs of specific end uses. At the conclusion of the crosslinking reaction the binder commonly is securely bound on the surfaces of the fibrous material in a concentration of approximately 1 to 50 (e.g., approximately 5 to 10) percent by weight of the fibrous material.

The binder composition of the present invention can be economically prepared and offers advantages over binder compositions that are commonly utilized in the prior art. The use of phenol-formaldehyde component is eliminated. The use of the polyamic acid component of the binding composition offers the following advantages over the use of polycarboxylic acids of comparable molecular weight: possible neutral pH of the resin solution, minimization of process corrosion, minimization of product corrosion, low surface tension and the better wetting of the fibrous surfaces, possible water repellency of the resin when cured, possible elimination of additives commonly used with polyacrylic acid binders, and the potential for utilization of renewable sources.

The following Examples are presented to provide specific representative embodiments of the present invention. It should be understood, however, that the invention is not limited to the specific details as set forth in the Examples. Example Nos. 1 and 11 are directed to the formation representative water-soluble polyamic acids for use in the binding composition. Examples Nos. 2 to 10, 12, and 13 exemplify the use of the water-soluble polyamic acid together with an organic crosslinking agent to bind a fibrous material and the resulting bound fibrous products.

EXAMPLE 1

To a flask equipped with a reflux condenser were added 400 grams of water and 113 grams of a 30 percent solution of ammonia. To this solution were added 480 grams of poly (styrene-maleic)anhydride having a molecular weight of approximately 2,000 with stirring until partially dissolved. The solution was next heated to 90° C. and was maintained at that temperature for two hours to produce a clear solution of water-soluble polyamic acid having both amide and carboxylic acid groups.

EXAMPLE 2

To 100 grams of the polyamic acid solution of Example 1 were added with stirring 10.0 grams of diethanolamine serving as an organic crosslinking agent that was capable of undergoing a covalent crosslinking reaction with the polyamic acid. The resulting aqueous solution, having a viscosity somewhat greater than that of Example 2, next was coated on fiberglass by means of a curtain coater while in a bat configuration, and the coated fiberglass was heated at 180° C. for 2 minutes to expeditiously achieve the curing and crosslinking of the polyamic acid to form a white, rigid, and highly water-resistant cured binder in association with the fiberglass wherein adjoining fibers were bound at cross-over points. The cured binder was present on the fiberglass in a concentration of approximately 6 percent by weight based on the weight of the fiberglass. Comparable results were obtained at a curing temperature of 200° C. as well as when 7.0 grams of diethanolamine crosslinking agent were utilized.

EXAMPLE 3

Example 2 was repeated with the exception that 10.0 grams of triethanolamine crosslinking agent were substituted for the diethanolamine crosslinking agent. Comparable results were achieved at a curing temperatures of 180° C. and 200° C. and when 15.0 grams of triethanolamine crosslinking agent were utilized.

EXAMPLE 4

Example 2 was repeated with the exception that 13.4 grams of trimethylol propane crosslinking agent were substituted for the diethanolamine crosslinking agent. Comparable results were achieved at curing temperatures of 180° C. and 200° C.

EXAMPLE 5

Example 2 was repeated with the exception that 13.6 grams of pentaerythrytol crosslinking agent were substituted for the diethanolamine crosslinking agent. A comparable extremely white, rigid, and highly water-resistant cured binder in association with the fiberglass was formed. Comparable results also were achieved at a curing temperature of 180° C.

EXAMPLE 6

Example 2 was repeated with the exception that 11.6 grams of hexanediamine crosslinking agent were substituted for the diethanolamine crosslinking agent. Generally comparable results were achieved at curing temperatures of 180° C. and 200° C. The resulting bound fiberglass product was rigid and highly water-resistant, and the coloration was off-white.

EXAMPLE 7

Example 2 was repeated with the exception that 6.2 grams of ethylene glycol crosslinking agent were substituted for the diethanolamine crosslinking agent. Comparable results were achieved at curing temperatures of 180° C. and 200° C.

EXAMPLE 8

Example 2 was repeated with the exception that 15 grams of triethylene glycol crosslinking agent were substituted for the diethanolamine crosslinking agent. Generally comparable results were achieved at curing temperatures of 180° C. and 200° C.; however, the product was less rigid and the water resistance in the bound fiberglass was slightly reduced.

EXAMPLE 9

Example 2 was repeated with the exception that 14.4 grams of water-soluble Michael adduct crosslinking agent having reactive hydroxyl end groups were substituted for the diethanolamine crosslinking agent. The Michael adduct crosslinking agent was formed by first dissolving 31.5 grams of diethanolamine which served as a Michael donor in 43 grams of water in a reaction zone, 11.6 grams of maleic acid which served as a Michael acceptor were slowly added with stirring while the temperature was maintained at 50° C., and the temperature next was raised to 90° C. where it was maintained for one hour to form the Michael adduct. A white rigid, and highly water-resistant cured binder in association with the fiberglass was formed wherein adjoining fibers were bound at cross-over points. Comparable results were obtained at a curing temperature of 200° C. as well as when 21.5 grams of the Michael adduct crosslinking agent were utilized.

EXAMPLE 10

Example 2 was repeated with the exception that 22 grams of a different water-soluble Michael adduct crosslinker were utilized than in the preceding Example 9. The Michael adduct in this instance was formed by first dissolving 21 grams of diethanolamine which served as a Michael donor in a 28 grams of water while present in a reaction zone, 7.2 grams of acrylic acid which served as a Michael acceptor were slowly added with stirring while the temperature was maintained at 50° C., and the temperature next was raised to 90° C. where it was maintained for one hour to form the Michael adduct. A white rigid, and highly water-resistant cured binder in association with the fiberglass was formed wherein adjoining fibers were bound at cross-over points. Comparable results were obtained at a curing temperature of 200° C.

EXAMPLE 11

To a flask equipped with a reflux condenser were added 315 grams of water and 75 grams of glycine (i.e., aminoacetic acid). To this solution were added 240 grams of poly(styrene-maleic)anhydride having a molecular weight of approximately 2,000 with stirring until dissolved. The solution was next heated to 90° C. and was maintained at that temperature for two hours to produce a clear solution of water-soluble polyamic acid having both amide and carboxylic acid groups.

EXAMPLE 12

To 111 grams of the polyamic acid solution of Example 11 were added with stirring 7.0 grams of diethanolamine serving as an organic crosslinking agent capable of undergoing a covalent crosslinking reaction with the polyamic acid. The resulting aqueous solution next was coated as earlier described on the fiberglass bat by means of a curtain coater, the coated fiberglass was heated at 180° C. for 3 minutes to expeditiously achieve the crosslinking of the polyamic acid and to form a white, rigid, and highly water-resistant cured binder in association with the fiberglass wherein adjoining fibers were bound at cross-over points. The cured binder was present on the fiberglass in a concentration of approximately 6 percent by weight. Comparable results were obtained at a curing temperature of 200° C. The modulus of the resulting rigid bound product was less than that of Example 2.

EXAMPLE 13

Example 12 was repeated with the exception that 10 grams of triethanolamine were substituted for the diethanolamine organic crosslinking agent. Comparable results were achieved at curing temperatures of 180° C. and 200° C. with the exception that the coloration of the resulting bound fiberglass product was off-white.

None of the foregoing binding compositions displayed a propensity to generate foam, all were non-corrosive, and prior to curing generally possessed reduced viscosities at comparable solids levels and better fiber wetting characteristics when compared to binding compositions based on the reaction of poly(styrene-maleic)anhydride having a molecular weight of approximately 2,000 and diethanolamine crosslinking agent in molar ratios of 1:1 and 1:1.3.

The principles, preferred embodiments, and modes of operation of the present invention have been described in the foregoing specification. The invention which is protected herein, however, is not to be construed as being limited to the particular forms disclosed, since these are regarded as being illustrative rather than restrictive. Variations and changes may be made by those skilled in the art without departing from the spirit of the invention.

What is claimed is:

1. A process for binding a fibrous material, the process comprising:
    applying to a surface of the fibrous material an aqueous binding composition to form a coated fibrous material, wherein the binding composition comprises:
    (a) a water-soluble polyamic acid formed by the reaction of:
    (i) a polycarboxylic acid or polyanhydride having a molecular weigh of at least 150 g/mol; and
    (ii) ammonia or an amine compound, and
    (b) an organic crosslinking agent capable of undergoing a covalent crosslinking reaction with the water-soluble polyamic acid when heated; and
    heating the coated fibrous material to crosslink the water-soluble polyamic acid with the organic crosslinking agent to form a cured binder, wherein one or more adjoining fibers of the fibrous material are bound to each other at cross over points by the cured binder.

2. The process of claim 1, wherein the fibrous material includes one or more type of fibers selected from the group consisting of mineral fibers, glass fibers, and polymeric fibers.

3. The process of claim 1, wherein the water-soluble polyamic acid is formed by the reaction of both the polycarboxylic acid and the polyanhydride with the ammonia or the amine compound.

4. The process of claim of claim 1, wherein the polycarboxylic acid or polyanhydride has a molecular weight of about 150 g/mol to about 1,000,000 g/mol.

5. The process of claim 1, wherein the polycarboxylic acid or polyanhydride has molecular weight of about 1000 g/mol to about 10,000 g/mol.

6. The process of claim 1, wherein the polycarboxylic acid or polyanhydride has molecular weight of about 1000 g/mol to about 5000 g/mol.

7. The process of claim 1 wherein the polyanhydride includes one or more polyanhydrides selected from the group consisting of polyacrylic anhydride, polymethacrylic anhydride, pyromellitic anhydride, poly(acrylic-co-methacrylic) anhydride, poly(acrylic-co-maleic)anhydride, poly(methacrylic-co-maleic)anhydride, polycrotonic anhydride, polymaleic anhydride, poly(styrene-maleic)anhydride, poly(ethylene-maleic)anhydride, poly(propylene-maleic)anhydride, poly(vinylether-maleic)anhydride, poly(butadien-maleic)anhydride, poly(acrylamide-maleic)anhydride, and malienated oils.

8. The process of claim 1, wherein the polycarboxylic acid comprises a homopolymer or copolymer of one or more organic acids selected from the group consisting of acrylic acid, methacrylic acid, maleic acid, fumaric acid, crotonic acid.

9. The process of claim 1, wherein the polyanhydride comprises poly(styrene-maleic anhydride.

10. The process of claim 9, wherein the poly(styrene-maleic) anhydride has a molecular weight of about 1000 g/mol to about 5000 g/mol.

11. The process of claim 1, wherein the water-soluble polyamic acid is formed by the reaction of the polycarboxylic acid or the polyanhydride with the ammonia.

12. The process of claim 1, wherein the amine compound is a primary amine or a secondary amine.

13. The process of claim 1, wherein the amine compound includes one or more amines selected from the group consisting of aliphatic amine compounds, aromatic amine compounds, aliphatic/aromatic amine compounds, and functionalized amine compounds.

14. The process of claim 1, wherein the amine compound comprises glycine.

15. The process of claim 1, wherein the organic crosslinking agent includes one or more crosslinking agents selected from the group consisting of polyols, polyamines, and polyalkanolamines.

16. The process of claim 1, wherein the organic crosslinking agent includes one or more crosslinking agents selected from the group consisting of glycols, glycol ethers, polyamines, alkanolamines, polyester polyols, polyether polyols, acrylic polyols, urethane polyols, polysaccharides, and polyvinyl alcohols.

17. The process of claim 1, wherein the organic crosslinking agent includes one or more crosslinking agents selected from the group consisting of diethanolamine, and triethanolamine.

18. The process of claim 1, wherein the water-soluble polyamic acid is formed by the reaction of poly(styrene-maleic)anhydride having to molecular weight of about 1000 g/mol to about 5000 g/mol and the ammonia, and
    wherein the organic crosslinking agent comprises one or more of polyols, polyamines, or polyalkanolamines.

19. The process of claim 1, wherein the organic crosslinking agent comprises a Michael adduct crosslinking agent having one or more reactive hydroxyl end groups formed by an addition reaction of:
    a Michael acceptor compound with alpha-beta unsaturation attached to an electron-withdrawing group; and
    a nucleophilic compound serving as a Michael donor capable of reaction with the Michael acceptor.

20. The process of claim 19, wherein the Michael acceptor compound is selected from the group consisting of ester groups, acid groups, amide groups, nitro groups, nitrile groups, ketone groups, aldehyde groups; and
    nucleophilic compound serving as the Michael donor is selected from the group consisting of alkylamines, alkanolamines, and thiols.

21. The process of claim 19, wherein the Michael the nucleophilic compound serving as a Michael donor comprises diethanolamine, triethanolamine, or mixtures thereof.

22. The process of claim 1, wherein the water-soluble polyamic acid is formed by the reaction of poly(styrene-maleic)anhydride having a molecular weight of about 1000 g/mol to about 5000 g/mol and the ammonia, and
    wherein the organic crosslinking agent is a Michael adduct formed by an addition reaction of:

a Michael acceptor compound with alpha-beta unsaturation attached to an electron-withdrawing group comprising acrylic acid, maleic acid, maleic anhydride, or mixtures thereof; and a Michael donor comprising mono- or dialkanolamines having two to four carbon atoms per alkanol group.

23. The process of claim 1, wherein the heating of the coated fibrous material is conducted at a temperature of about 160° C. to about 250° C.

24. The process of claim 1, wherein the heating of the coated fibrous material is conducted at a temperature of about 200° C.

25. The process of claim 1, wherein the cured binder comprises about 1 wt. % to about 50 wt. % of a weight of the fibrous material.

26. A process of making a fiber-reinforced composite, the process comprising:

reacting a polyanhydride with ammonia to form a polyamic acid;

mixing the polyamic acid with an organic crosslinking agent to form an uncured hinder solution;

applying the uncured binder solution to a group of fibers to form an uncured fiber composite; and heating the uncured fiber composite to cure the uncured binder solution and form the fiber-reinforced composite.

27. The process of claim 26, wherein the polyanhydride comprises poly(styrene-maleic)anhydride.

28. The process of claim 27, wherein the poly(styrene-maleic)anhydride has a molecular weight of about 2000 g/mol.

29. The process of claim 26, wherein the crosslinking agent comprises diethanolamine.

30. The process of claim 26, wherein the crosslinking agent comprises hexanediamine.

31. The process of claim 26, wherein the uncured binder solution is applied to the group of fibers by curtain coating.

32. The process of claim 26, wherein the uncured fiber composite is heated to a temperature of about 180° C. to about 200° C.

33. The process of claim 26, wherein the group of fibers comprises a mat of glass fibers, and the fiber-reinforced composite comprises a glass-fiber reinforced mat.

34. A process of making a fiber-reinforced composite, the process comprising:

reacting a polyanhydride with an amine to form a polyamic acid;

mixing the polyamic acid with an organic crosslinking agent to form an uncured binder solution;

apply the uncured binder solution to a group of fibers to form an uncured fiber composite; and heating the uncured fiber composite to cure the uncured binder solution and form the fiber-reinforced composite.

35. The process of claim 34, wherein the amine comprises glycine.

* * * * *